United States Patent [19]
Bonnema et al.

[11] Patent Number: 5,928,605
[45] Date of Patent: *Jul. 27, 1999

[54] DEVICE FOR DISPENSING A VOLATILE SUBSTANCE

[75] Inventors: James Bonnema, Middleton; Wen Der Wang, Wilmington, both of Mass.; Scott W. Demarest; Paul E. Furner, both of Caledonia, Wis.; Donald W. Hildebrandt, Yorkville, Wis.

[73] Assignee: The Schawbel Corporation, Boston, Mass.

[*] Notice: This patent is subject to a terminal disclaimer.

[21] Appl. No.: 08/994,424

[22] Filed: Dec. 19, 1997

Related U.S. Application Data

[63] Continuation-in-part of application No. 08/506,555, Jul. 25, 1995, Pat. No. 5,700,430, and a continuation-in-part of application No. 08/834,727, Apr. 1, 1997.

[51] Int. Cl.$^6$ .................................................. A61L 9/03
[52] U.S. Cl. .............................. 422/5; 422/125; 422/306; 239/56; 126/401; 431/7; 431/239
[58] Field of Search .................................... 422/125, 305, 422/306, 4, 5; 239/56; 126/401; 431/7, 329

[56] References Cited

U.S. PATENT DOCUMENTS 5,394,862 3/1995 Firatli et al. .
5,700,430 12/1997 Bonnema et al. ...................... 422/125

Primary Examiner—Elizabeth McKane
Attorney, Agent, or Firm—Levisohn, Lerner, Berger & Langsam

[57] ABSTRACT

A device for dispensing a volatile substance includes a gas-fueled, portable heat source. The device includes a catalyst support structure to flamelessly combust liquid or gaseous fuel and thereby provide a lower temperature heat source than a heat source that combusts fuel via flame. The fuel is ignited inside the catalytic support structure by a spark electrode. A spark jumps from the electrode to an interior surface of the structure and ignites the fuel inside the structure, causing a flame to propagate. The flame heats the catalytic structure to an activation temperature, after which the fuel is combusted flamelessly on the surface of the catalytic structure. The device includes a heating plate for heating the volatile substance and for receiving heat from the catalytic structure. A heat box substantially surrounds the catalytic structure and heating plate. The heat box has a window through which volatile substances released from the heating plate may escape. The device also has a housing within which the heat box is held in spaced relation from the housing, the housing having a housing window adjacent to the heat box window. By use of the device, the catalytic structure heats the heating plate to volatilize a volatile substance placed thereon, which may then escape into the atmosphere through the heat box window, with the housing remaining cool.

36 Claims, 7 Drawing Sheets

DEVICE FOR DISPENSING A VOLATILE SUBSTANCE

RELATED APPLICATIONS

This application is a continuation-in-part of both U.S. patent application Ser. No. 08/506,555, filed Jul. 25, 1995, now U.S. Pat. No. 5,700,430, and pending U.S. patent application Ser. No. 08/834,727, filed Apr. 1, 1997.

BACKGROUND OF THE INVENTION

1. Field of the Invention

The present invention relates generally to devices for dispensing volatile active substances. More particularly, the invention relates to portable, gas-fueled devices that utilize heat to dispense volatile substances into the air.

2. Description of Related Art

The art has produced a variety of portable devices for dispensing volatile substances into the air. Such volatile substances most commonly are either insect control active ingredients or air treatment materials, such as air fresheners. Many of these portable devices utilize a battery-powered fan to evaporate volatilizable materials, without the use of heat.

Devices that utilize heat to evaporate or volatilize an active ingredient or other volatile substance are also well known in the art. However, many of these devices require access to house current or the like for the electrical power required to energize the heater. Consequently, the devices are not portable beyond the length of their power cords from the electrical receptacle into which they must be plugged.

Flames are another common source of heat for dispensing volatile substances. For example, scented candles and lighted wicks of various sorts underneath potpourri kettles are traditional devices for air freshening or air scenting. Citronella candles are an example of the same technique applied to insect control. Similarly, mosquito coils use combustion heat to volatilize or otherwise distribute insect control active ingredients into the area surrounding the device. A mosquito coil is a structure of punk or other slow-burning material that is either self-supporting or that is printed onto a substrate. The punk is lighted at one end to slowly burn, like incense, distributing with its smoke or by volatilization an insect control ingredient.

Other devices burn liquid fuel, most commonly alcohol, to generate heat for vaporizing insect control active ingredients. The device distributed by La Reina Enterprises of Falmouth, Mass. under the name "Skeeter Eater" evaporates insect repellent from an impregnated pad by heating the pad with a hot metal catalyst mesh fueled with alcohol. Similar products, sometimes using a simple alcohol flame instead of a metal catalyst mesh, are sold in Europe and Japan by other companies. The insect repellent pads of the Skeeter Eater device are flat and rectangular. The device has a flat bed, which is bridged over by a grid. A user slides a repellent pad onto the bed from an opening at one side of the grid and may retrieve it from a comparable opening at the opposite side of the bed. The liquid fuel devices generally require a user to pour fuel prior to using the device, with the consequent danger of spilling flammable liquids. Such spillage presents both a fire hazard and a mess, especially in devices that are lit with a match or other open flame.

Although these devices and methods exist in the art, being referred to by way of example only, the art is still in need of a safe and easy to use device that is not limited by the need to be plugged into an electrical receptacle, being instead entirely portable for use at any location desired. The art is also still in need of a combustion-heated device for volatilizing an active ingredient where that device requires no unguarded or accessible flame that could ignite flammable materials in the area and also operates with the adjustability, cleanliness, freedom from odor, and reliability associated with electrical devices.

BRIEF SUMMARY OF THE INVENTION

The device of the invention for dispensing a volatile substance includes a gas-fueled, portable heat source having tank connection means to receive a fuel tank or fuel cartridge in gas-tight relation, a combustion nozzle, and means for metering fuel from the fuel tank to the combustion nozzle to fuel a flame at the nozzle. Either a refillable fuel tank or a reusable or replaceable fuel cartridge may be used. The device further includes a sole plate having a heated surface for heating the volatilizable substance and heat transfer means for enclosing the combustion nozzle and transferring heat from the flame to the sole plate. A heat box substantially surrounds the heat transfer means and sole plate. The heat box is made of materials capable of withstanding the heat radiating therefrom and has a window through which volatile substances released from the sole plate may escape the heat box. The device also has a housing having interior surfaces that define an interior chamber within which the heat box is held in spaced relation from the housing. The housing includes a housing window that is adjacent to the heat box window. By use of the device, a flame may be sustained at the combustion nozzle to heat the sole plate to volatilize a volatile substance placed on the heated surface, which volatilized substance may then escape into the atmosphere through the heat box window, with the housing remaining cool relative to the temperature of the flame, heat transfer means, and sole plate.

In an alternative embodiment, the inventive device for dispensing a volatile substance includes a portable heat source having a tank connector to receive a fuel tank in gas-tight relation, a catalytic heater, and a fuel metering device for allowing fuel under pressure to flow from the fuel tank to the catalytic heater to fuel flameless combustion at the catalytic heater. A heating plate receives heat from the catalytic heater; the heating plate has a heated surface for heating the volatile substance. A heat box substantially surrounds the catalytic heater and heating plate. The heat box is made of materials capable of withstanding the heat radiating therefrom and has a window, through which volatile substances released from the heating plate may escape the heat box. The device possesses a housing having interior surfaces that define an interior chamber within which the heat box is held in spaced relation from the housing. The housing includes a housing window that is adjacent to the heat box window. Flameless combustion may be sustained on the catalytic heater to heat the heating plate to volatilize a volatile substance placed on the heated surface. The volatilized substance may thus escape into the atmosphere through the heat box window. The housing remains cool relative to the temperature of the catalytic heater and the heating plate.

The method of the invention for dispensing a volatile substance into the atmosphere includes the steps of providing a gas-fueled, portable heat source adapted to fuel a flame at a combustion nozzle; providing a sole plate having a heated surface for heating the substance to be volatilized; providing heat transfer means for transferring heat from the flame of the combustion nozzle to the sole plate; and providing a heat box that substantially surrounds the heat transfer means and sole plate, the heat box being made of materials capable of withstanding the heat radiating therefrom and having a window through which volatile substances from the sole plate may escape the heat box. By the method of the invention, a flame may be sustained at the combustion nozzle to heat the sole plate and volatilize volatile substances placed on the heated surface, which may then escape through the heat box window to be dispensed into the atmosphere.

In an alternate embodiment, the inventive method for dispensing a volatile substance into the atmosphere includes the steps of providing a gas-fueled, portable heat source adapted to fuel flameless combustion on a catalytic heater; providing a heating plate having a heated surface for heating the substance to be volatilized, the heating plate receiving heat from the catalytic heater; and providing a heat box that substantially surrounds the catalytic heater and heating plate, the heat box being made of materials capable of withstanding the heat radiating therefrom and having a window through which volatile substances from the heating plate may escape the heat box. Flameless combustion may be sustained on the catalytic heater to heat the heating plate and volatilize volatile substance placed on the heated surface, which may then escape through the heat box window to be dispensed into the atmosphere.

The embodiments of the invention, both the method and the apparatus, that utilize a catalytic heater to achieve flameless combustion are particularly advantageous for several reasons. First, because the flameless combustion is occurring inside a catalytic structure, the combustion will not be inadvertently terminated or interrupted. This feature is well-suited for outdoor use where breezes are common that would otherwise be able to blow out a flame, such as the flame of a Citronella candle or even a butane combustion flame. Moreover, catalytic (i.e., flameless) combustion occurs at much lower temperatures than a typical flame; catalytic combustion occurs in the range of 400–500° C., whereas a butane flame is typically 1700° C. By combusting the fuel at significantly reduced temperatures, several further advantages are realized. It becomes easier and less expensive to shield the outer housing and keep it cool and thus safe to the touch. Additionally, the heating plate that transfers heat from the combustion source to the to-be-volatized chemical can be much thinner, using less material and costing less in manufacturing. As a result, the heating plate will reach its target temperature faster, and the device will thus have a shorter warm-up period.

DETAILED DESCRIPTION OF THE PREFERRED EMBODIMENTS

Figure 1:
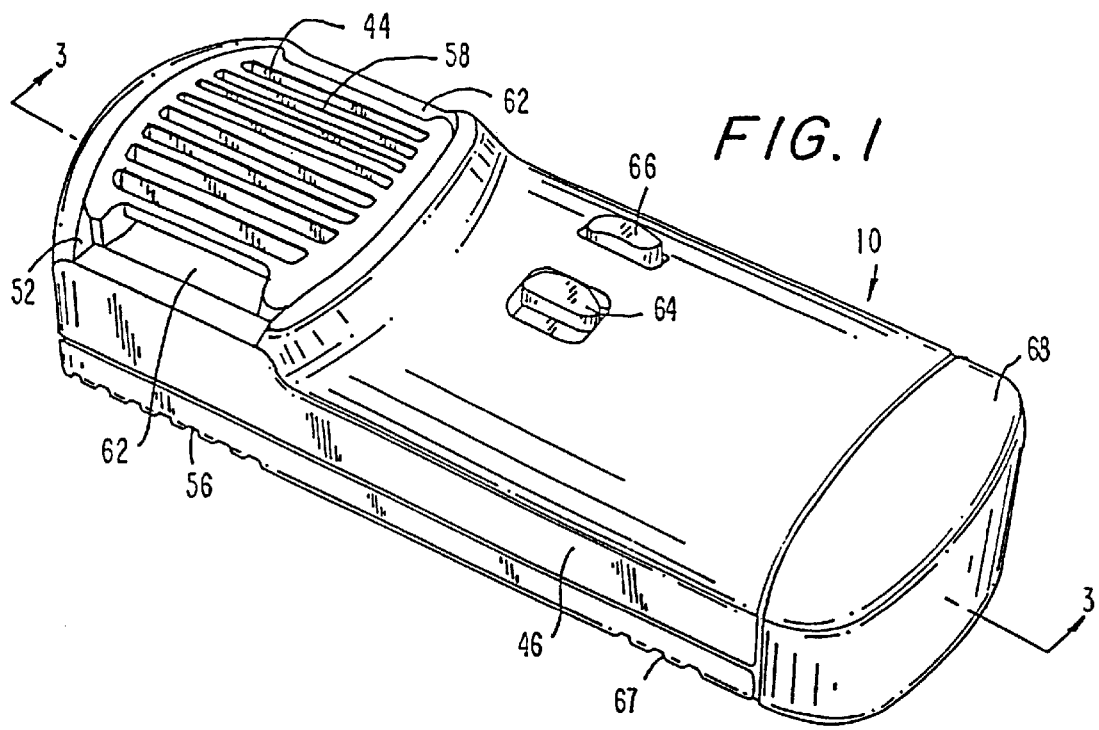
FIG. 1 is a perspective view from the foot end and from above and to the right side of the device of the invention for dispensing a volatile substance.
Figure 2:
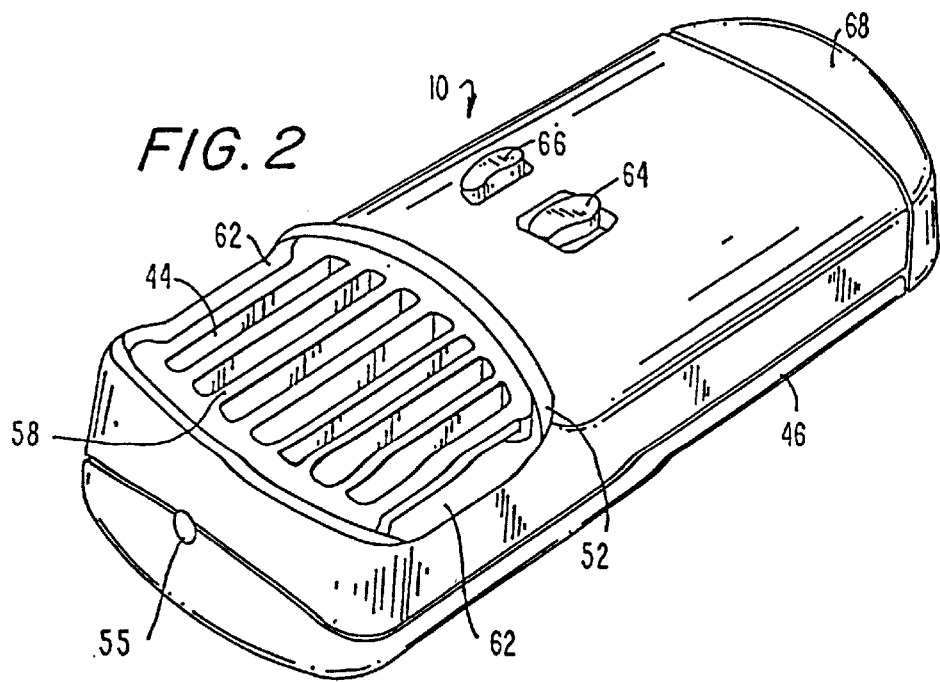
FIG. 2 is a perspective view from the head end and from above and to the right side of the device of FIG. 1.
Figure 3:
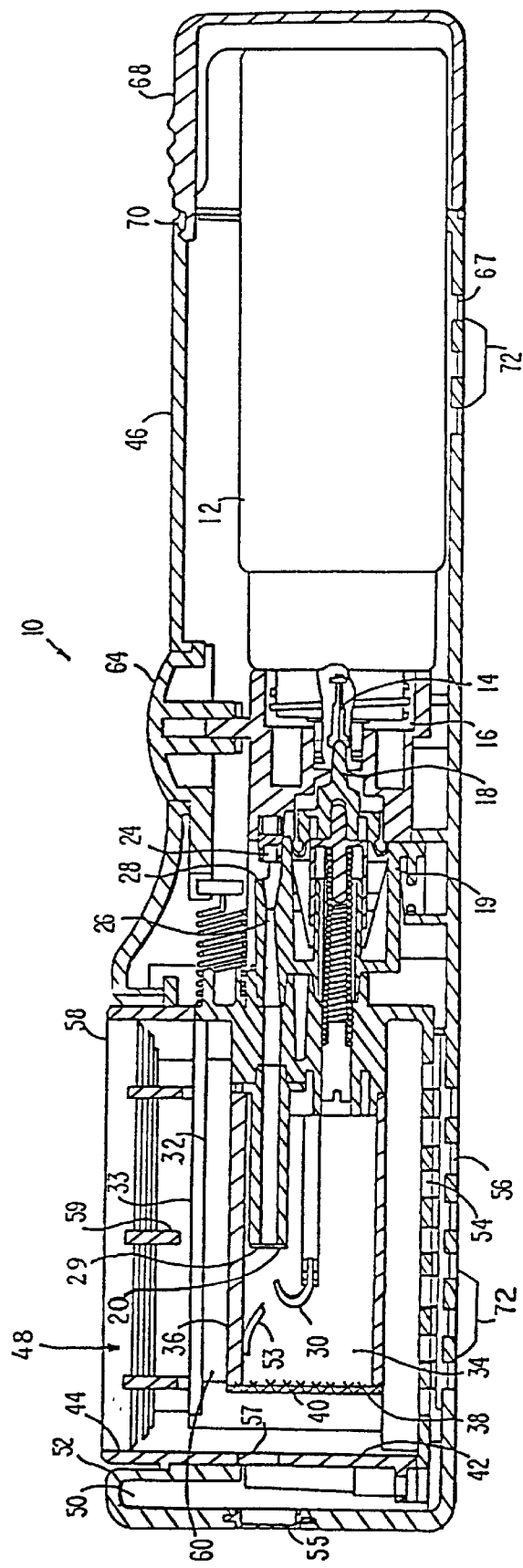
FIG. 3 is a cross-sectional view of the device of FIG. 1 taken along section lines 3—3 of FIG. 1.

Turning now to the drawings, wherein like parts are indicated by like reference numbers, a first preferred embodiment of the device of the invention for dispensing a volatile substance is shown in FIGS. 1 to 3 at reference number 10. The device 10 utilizes a gas-fueled, portable heat source. The heat source has tank connection means to receive a fuel tank in gas tight relation. The heat source also includes a combustion nozzle, at which location the gas burns, and means for metering fuel from the fuel tank to the combustion nozzle to fuel the flame at the nozzle. The preferred mechanism for the gas-fueled portable heat source is substantially identical that in U.S. Pat. No. 4,669,123 issued Oct. 13, 1987 and entitled PORTABLE HEATING APPLIANCE. U.S. Pat. No. 4,669,123 is incorporated herein by reference as are U.S. Pat. Nos. 4,759,343 and 4,815,441. Those patents describe a two burner system while the present invention has a single burner system. In all other respects, operation of the fuel system regulator, gas flow, ignition and operation is substantially identical.

The preferred embodiment of the portable heat source shown in FIG. 3 thus utilizes a fuel tank 12 having a fuel tank valve 14. Tank connection means 16 is adapted to threadedly engage corresponding threads on the fuel tank 12 to hold the fuel tank in place. Bayonet, snap, and other alternatives to threaded engagement will be apparent to one skilled in the art and are within the breadth and scope of the invention. When the tank connection means 16 has engaged the fuel tank 12, a valve activator 18 depresses the fuel tank valve 14, releasing gas from within the fuel tank into the device 10. Pressure regulator 19 controls the flow rate of gas and may be adjustable with conventional means to adjust the flow rate.

The heat source further includes a combustion nozzle 20. Means for metering fuel from the fuel tank 12 to the combustion nozzle 20 is provided, in accord with the disclosure of U.S. Pat. No. 4,669,123. The gas from the fuel tank 12 is released through a gas orifice 24 and thereby directed into a venturi 26, where it is accelerated. Air is mixed with the gas as it enters the venturi 26, the air entering through an air inlet 28 located just up-stream of the venturi. The air and gas mixture exits the combustion nozzle 20, which is covered by a nozzle screen 29. A piezoelectric igniter 30 provides a spark to ignite the gas and air mixture, which burns at the combustion nozzle 20 as a flame confined to the nozzle screen 29.

The preferred portable heat source just described accommodates the use of butane, which is a convenient and reliable fuel. Furthermore, the fuel tank 12 is conveniently removable by unscrewing it from the tank connection means 16, allowing for the attachment of a fresh tank to refuel the device. Nevertheless, the invention is not confined to this particular gas-fueled, portable heat source. Instead, alternative mechanisms and arrangements are possible, as will be apparent to one skilled in the art. Such alternatives, including, by way of example only, refillable or one-use fuel tanks, alternative means for metering fuel, and the like, are within the scope and breadth of the invention.

Figure 4:
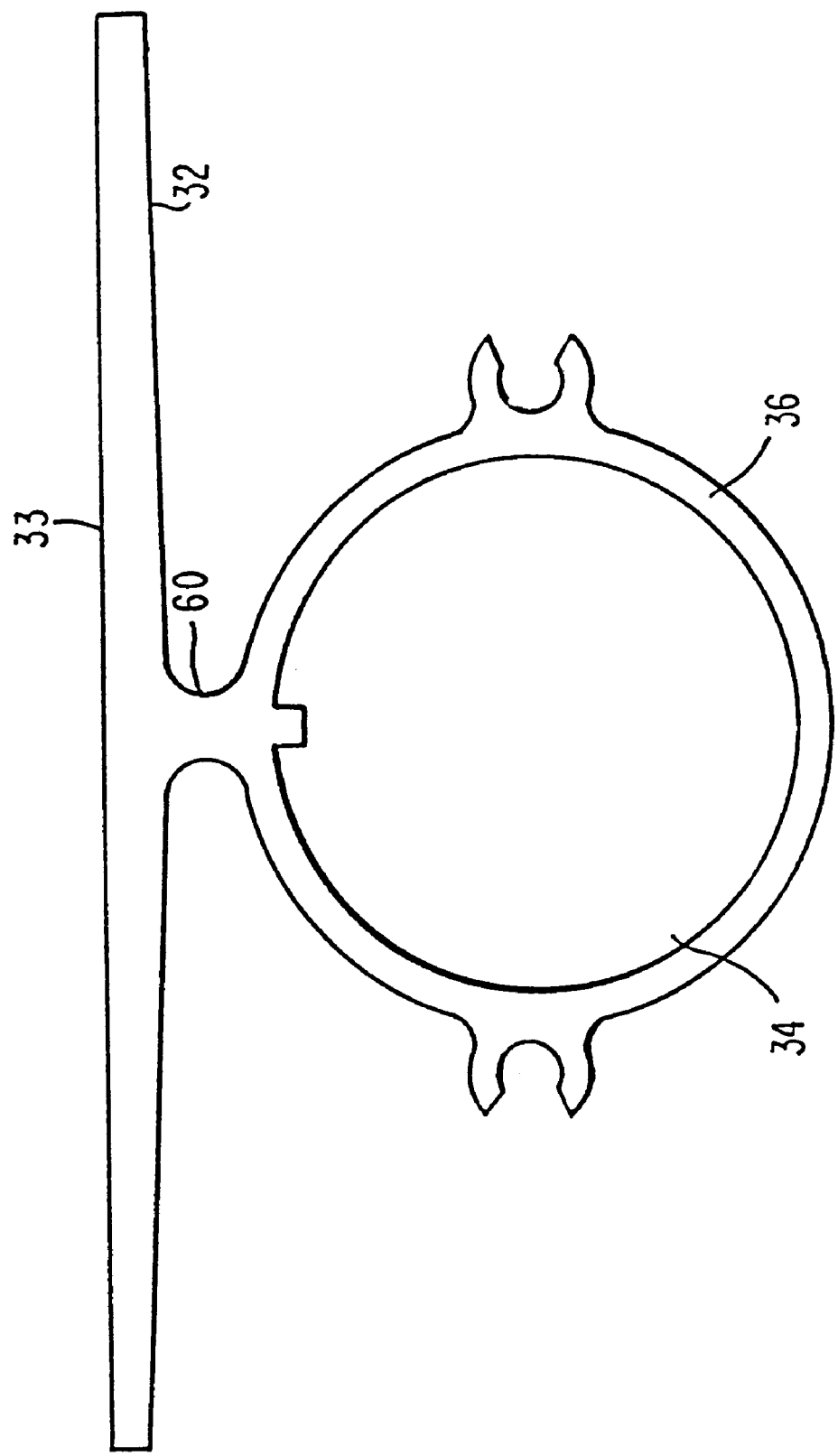
FIG. 4 is an end elevational view of the heat exchanger of the device of FIG. 1 that combines the sole plate and combustion chamber thereof.

The device 10 of the invention for dispensing a volatile substance further includes a sole plate 32 having a heated surface 33 for heating the volatile substance. These structures are shown in FIGS. 3 and 4. The sole plate 32 may be maintained at a broad range of temperatures by adjusting the size of the flame at the combustion nozzle 20 and by other means described below. Useful temperature ranges for the sole plate 32 extend from as low as about 50° C. (useful for certain air treatment materials, for example) to as high as about 280° C. (useful, for example, for triggering certain blowing agents for fumigators). A preferred temperature range useful for volatilizing certain insect control active ingredients is about 125 to 200° C. Indeed, this temperature range is practical and useful for a variety of available insect control and air treatment active ingredients. Higher temperatures become more difficult to control. Lower temperatures may fail to volatilize active ingredients in amounts sufficient to be of practical use.

The sole plate 32 and its heated surface 33 may be of any convenient size or shape, including sharply curved, irregular, or angular shapes. However, it is presently preferred that the heated surface 33 and the sole plate 32, itself, be substantially planar, which term shall be understood to include gently curving surfaces and structures as well as rimmed or textured surfaces and the like.

The invention includes heat transfer means for enclosing the combustion nozzle 20 and transferring heat from a flame burning at that nozzle to the sole plate 32, the heat transfer means and sole plate, in combination, being referred to herein as the heat exchanger of the device. In the preferred embodiment, the heat transfer means is made of heat-conductive material and includes a combustion chamber 34. The combustion chamber 34 substantially encloses the combustion nozzle 20. Although the combustion chamber 34 may have any convenient shape, in the preferred embodiment, the combustion chamber is generally cylindrical, with its longitudinal axis extending generally parallel to the direction of gas flow from the combustion nozzle 20.

The combustion chamber 34 is connected to the sole plate 32 in thermally conductive relation. In the preferred embodiment, the combustion chamber has heat conductive chamber walls 36. At least one pressure release port 38 extends through the chamber walls 36 to provide a means for releasing the pressure that would otherwise build up from the introduction into the combustion chamber of the gas and air mixture flowing from the combustion nozzle 20. A flame arrester prevents the escape of flame from the combustion chamber 34. Any conventional flame arresting means may be used. However, the preferred form of flame arrester is a screen such as that shown at 40 in FIG. 3. The screen 40 permits the substantially unobstructed passage of air through the pressure release port 38. However, should the device 10 be conveyed into an explosive atmosphere, the screen 40 is adapted to confine combustion within the combustion chamber 34, much in the manner of a miner's lamp, thus preventing the escape of flame from the combustion chamber.

The walls 36 of the combustion chamber 34 may include outwardly extending radiators (not shown) or other means that will be apparent to one skilled in the art to dissipate excess heat. Such radiators and the size, shape, and geometry of the sole plate 32, together with various other means to ventilate, divert, or dissipate excess heat, all may be used to adjust the temperature of the heated surface 33 of the sole plate 32.

In the device 10 of the invention, a heat box 42 substantially surrounds the heat exchanger. The heat box 42 is made of materials capable of withstanding the heat radiating from the heat exchanger. Thus, as is shown in the preferred embodiment of FIG. 3, the heat box 42 encloses the combustion chamber 34 as well as the sole plate 32.

The heat box 42 has an outwardly opening window 44. Although side or other orientations for the heat box window 44 are possible, preferably the heat box window is located above the heated surface 33 of the sole plate 32 Volatile substances heating on the heated surface 33 may escape into the atmosphere through the window.

The device 10 of the invention further includes a housing 46. As is best seen in FIG. 3, the housing 46 has interior surfaces that define an interior chamber 48 within which the heat box 42 is held. The heat box 42 is held within the interior chamber 48 in spaced relation from the housing 46. Consequently, an air gap 50 exists that substantially separates the heat box 42 from the interior surfaces of the housing 46. The housing 46 includes a housing window 52 that is adjacent to and, preferably, open over and above the heat box window 44, leaving the heat box window unobstructed by the housing.

Preferably the heat box 42 includes at least one heat box vent 54 at a location lower than the heat box window 44, and the housing 46 includes a housing vent 56 preferably at a location no higher than the level of the heat box vent 54. In the preferred embodiment shown in FIGS. 1–3, the heat box and housing vents 54 and 56 are located at the under side of the heat box 42. By means of the heat box and housing vents 54, 56 a convection current may form when a flame is ignited at the combustion nozzle 20, which aids in the escape of volatile substances from the heat box window 44. Preferably the housing vent 56 is offset from or purposefully misaligned with the heat box vent 54 so that straight-line access through the vents to the heat exchanger is restricted. This arrangement is clearly seen in FIG. 3.

Preferably a glow wire 53 is positioned within the combustion chamber 34 at such a location that it is heated to a glowing temperature by the flame of the combustion nozzle 20. The glow wire 53 is shown in FIG. 3. The igniter 30 includes a glow wire and the housing 46 includes an observation window 55 and the heat box 42 includes an observation port 57, the observation window and port being so located that a user of the device 10 of the invention may observe therethrough the glowing state of the igniter 30. By this means, a user can readily find out by a visual check if a flame is burning at the combustion nozzle 20.

It is preferred that the heat box window 44 be closed with an air-transmitting grille such as that shown in the preferred embodiment at 58, most easily understood from FIGS. 1 and 2. The grille 58 is spaced above the heated surface 33 of the sole plate 32 sufficiently far as to withstand the heat therefrom. However, if the grille 58 is spaced too far above the heated surface 33, the grille can remain cool enough that volatile substance leaving the heated surface condenses on the underside of the grille. Consequently, it is essential to carefully adjust the distance between the grille 58 and heated surface 33, a distance that may have to be determined empirically. Preferably, the grille 58 includes at least one rib 59 extending toward the heated surface 33 for a selected distance such that the rib urges a volatile carrier (described below) placed under the grille toward contact with the heated surface 33. The rib 59 is shown in FIG. 3.

In this preferred embodiment, the combustion chamber 34 is a hollow cylinder connected to the underside of the sole plate 32 by a heat transfer rib 60 that extends for substantially the length of the combustion chamber, the heat transfer rib being shown in end view in FIG. 4. This arrangement allows for efficient heat transfer from the combustion chamber 34 to the sole plate 32 and also allows the combustion chamber, sole plate, and heat transfer rib 60 to be formed by extrusion, unitarily, out of aluminum, another appropriate metal or alloy, a heat conductive ceramic, or the like. When the heat transfer rib 60 attaches to the centerline of the sole plate 32, as in the embodiment shown, heat conducted from the combustion chamber 34 enters the sole plate at that location.

By this arrangement, a heat gradient may be generated across the heated surface 33 of the sole plate 32 when a flame is burning at the combustion nozzle 20, with the highest sole plate temperatures being generally centrally located on the heated surface. In such an instance, it is desirable that the grille 58 that closes the heat box window 44 be curved upwardly above the heated surface 33, with the greatest distance from the grille to the heated surface being above the hottest, central location on the heated surface. By this arrangement, illustrated in the Figures, in spite of the differing temperatures involved, each part of the grille 58 may be spaced above the heated surface 33 sufficiently far as to withstand the heat therefrom but remain close enough to be heated sufficiently that volatile substance leaving the heated surface does not condense on the grille.

In an alternative preferred embodiment, the combustion nozzle may be replaced by a catalytic, i.e., flameless, combustion mechanism. In such a mechanism, the catalytic substrate is a perforated metal or wire screen structure that will allow gases to pass freely through it. Preferably, the metal cylinder is perforated over only one portion, thereby forming perforated and non-perforated areas. The substrate is preferably closed such that it has no openings larger than one of the perforations or screen pores, and one end of the ignition spark electrode is located inside this enclosure. The perforated metal will not allow flame to pass through itself, so the catalytic heater is self-flame-arresting, requiring no other explosion protection. The catalytic structure is preferably cylindrical, with the perforated and catalyzed metal forming the periphery of the cylinder. One end of the cylinder is closed with a solid piece of material which contains an ignition electrode and an insulator to electrically insulate the electrode from the substrate. The other end of the cylinder is closed with a wire mesh screen or alternatively perforated metal. A fuel/air mixture is introduced through the screened end of the cylinder. The size of the screen is adjusted to the flow rate of fuel and air such that a sustained flame will initially burn on the burner screen inside the substrate. Preferably, the burner screen is located at a point in the catalyst structure between perforated and non-perforated portions.

When a voltage is applied between the electrode and the substrate, a spark jumps between the electrode and the nearest point on the substrate. Assuming the fuel/air mixture is correct, the spark ignites a blue flame which burns on the screen. If no catalytic material were present, the flame would burn in a continuous and sustained manner (as in the previous embodiment that utilizes combustion by flame), as fresh fuel and primary intake air are introduced through the screen, exhaust products leave through the perforated substrate, and external or secondary combustion air enters through the substrate. By introducing the catalytic material (platinum, palladium, etc.), some of the fuel air mixture in the area of the flame will combust catalytically, and the exhaust products of this catalytic reaction will poison and extinguish the flame. The catalytic reaction then spreads over the catalytic substrate such that all of the fuel/air mix will be combusted on the catalyst. In actual operation, it may take a few seconds from the time of the spark until the catalytic reaction has extinguished the flame and spread over the substrate.

Figure 5:
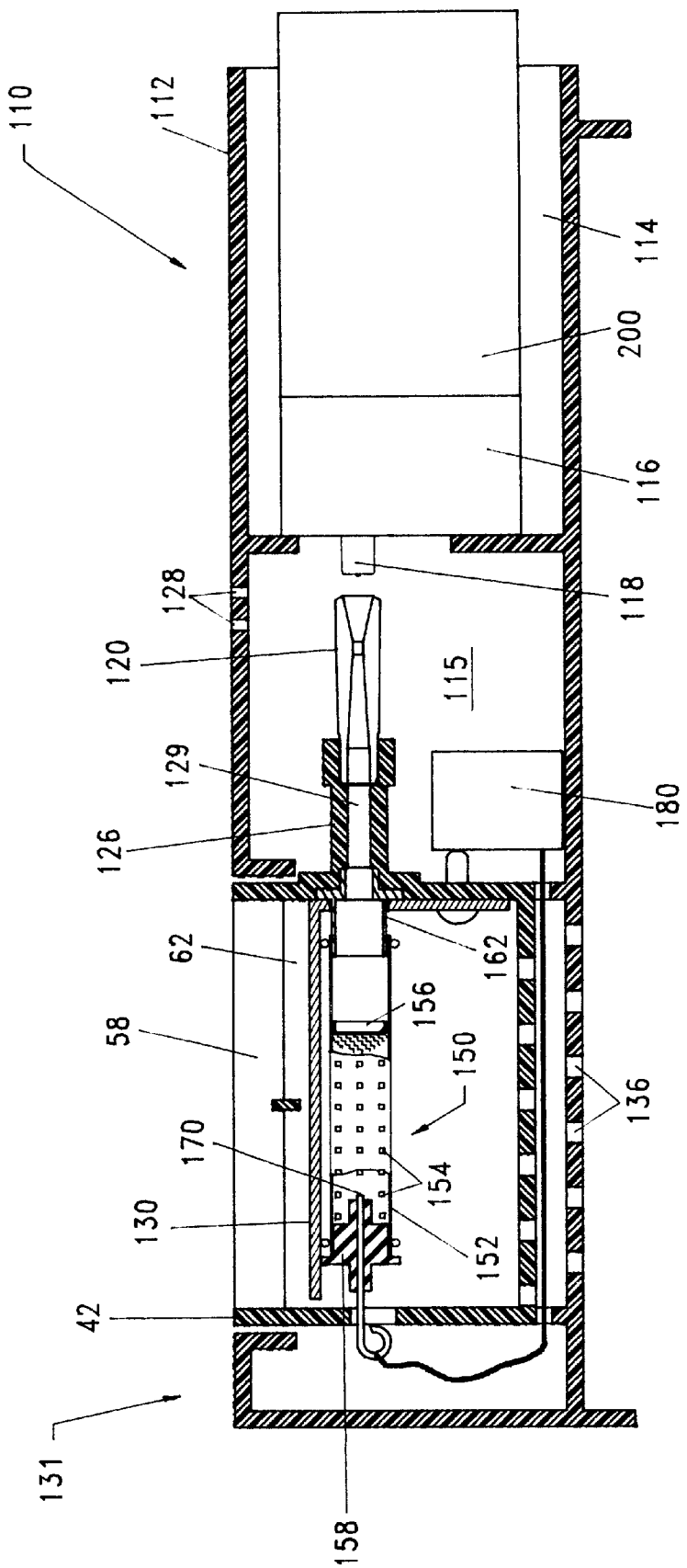
FIG. 5 is a cross-sectional view of an alternate embodiment of the invention employing a catalytic heater as a heat source.

As shown schematically in FIG. 5, housing 112 contains the fuel flow path from the fuel cartridge 200. Fuel cartridge 200 typically contains a gaseous or liquid fuel such as butane or propane, and fits into recess 114 of housing 112. Threads may be provided in recess 114 to mate with threads on cartridge 200 to lock the cartridge in place. Alternatively, instead of receiving a pre-filled fuel cartridge, housing 112 may be provided with a fillable fuel chamber (not shown) into which fuel would be added. Housing 112 is substantially hollow and has main cavity 115 in which the majority of the fuel flow path is disposed.

Inside cavity 114 in communication with fuel cartridge 200 is flow control device 116, which in this example is a known single stage pressure regulator, which could be similar to the single stage pressure regulator described in U.S. Pat. No. 4,699,123 to Zaborowski, the teachings of which are hereby incorporated by reference. Flow control device 116 regulates the flow of fuel from fuel cartridge 200 to the rest of the appliance. In some cases, the mere attachment of fuel cartridge 200 initiates the flow of fuel from the cartridge through flow control device 116. In other cases, a valve (not shown) may be opened manually by the user. In either event, when fuel pressure has built up to a certain level, fuel passes through flow control device 116 and exits from a small opening in gas jet 118. Gas jet 118 is in communication with the entrance of venturi tube 120, however it is not sealingly engaged with venturi tube 120. That is, the entrance of venturi tube 120 is open and exposed to cavity 115 of housing 112, so that when fuel from gas jet 118 enters the venturi tube, air is entrained along with the fuel to produce a fuel/air mixture that enters venturi tube 120. Air vents 128 formed in housing 112 allow cavity 115 of housing 112 to communicate with ambient air, and allow air to enter cavity 115 and mix with fuel from gas jet 118.

Attached to one end of venturi 120 is a projection 126. Projection 126 includes a central passageway 129 that allows the fuel/air mixture exiting from venturi tube 120 to travel to the rest of the appliance for combustion purposes. Projection 126 and passageway 129 may be integral with the housing, or they may be integral with heat box 42 as shown in FIG. 5.

Figure 6:
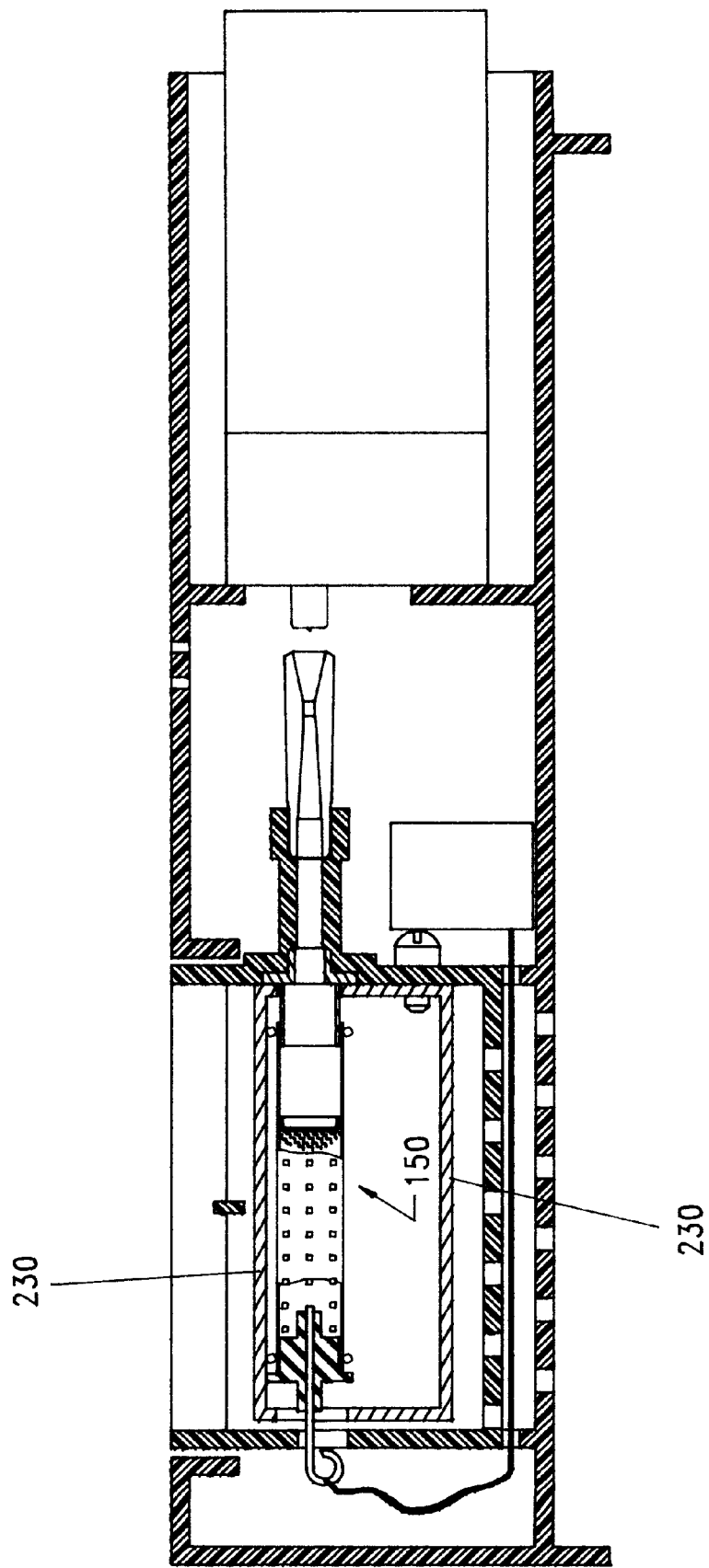
FIG. 6 is a cross-sectional view of the embodiment of FIG. 5 employing an alternate heating plate.
Figure 7:
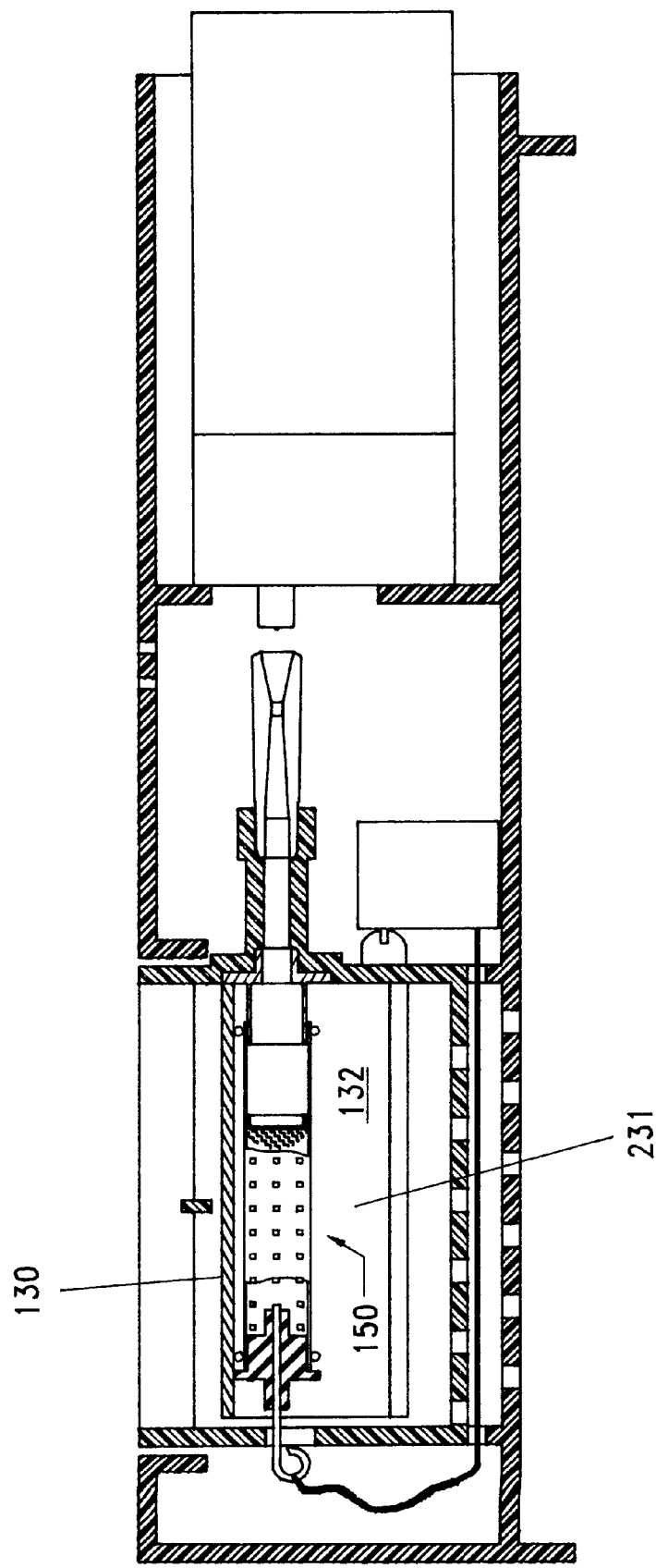
FIG. 7 is a cross-sectional view of the embodiment of FIG. 5 employing another alternate heating plate.
Figure 8:
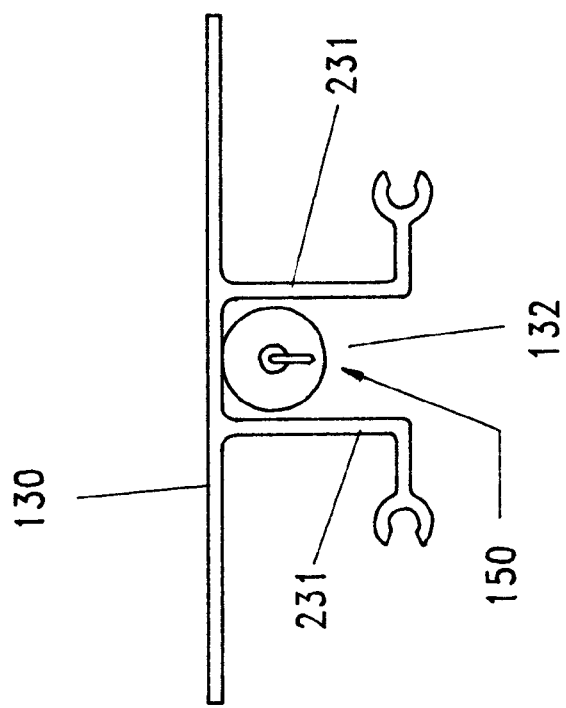
FIG. 8 is an end view of the catalytic heater and heating plate of FIG. 7.

Metal plate 130 is disposed in a distal end 131 of housing 112 and functions as the sole or heating plate in this embodiment. Plate 130 includes the main surface through which heat is transferred from the combustion of the fuel/air mixture to the volatile substance. It should therefore be a good conductor of heat. Secondary air vents 136 are provided in the distal end to allow ambient air to communicate with the interior of the barrel, and to allow the products of combustion of the fuel/air mixture to escape from the interior of the barrel. Metal plate 130 is depicted as being a flat plate disposed above catalytic assembly 150 in FIG. 5. In an alternative arrangement as depicted in FIGS. 7–8, metal plate 130 includes downwardly extending walls 231 which form a channel 132; catalytic assembly 150 is disposed in channel 132, as best shown in FIG. 8. In another alternative arrangement, as shown in FIG. 6, a metal box 230 is provided instead of metal plate 130. Metal box 230 includes a top plate, two side plates, and a bottom plate which substantially surround and enclose the catalytic heater. One or more side walls (e.g., the walls parallel to the plane of the page) may be omitted for ventilation.

Catalytic assembly 150, responsible for the flameless combustion of the fuel, is disposed in distal end 131 of housing 112. The assembly is in communication with passageway 129 of projection 126, so that the fuel/air mixture exiting from venturi tube 120 is fed through to the interior of the assembly via mounting tube 162.

The catalyst assembly 150 includes catalytic support 152, a metallic preferably tubular substrate on which a catalytic material such as palladium is disposed on at least an inner surface. One end of support 152 is in communication with mounting tube 162 so as to allow the fuel/air mixture to proceed to the combustion zone of the device. Perforations 154 are made in catalytic support 152 which allow the products of combustion formed inside support 152 to escape. However, the perforations are small enough to prevent flames from exiting the support. As illustrated in FIG. 5, perforations 154 are only provided on a portion of support 152. At or near the point where perforations 154 end is disposed a burner nozzle preferably in the form of a wire mesh burner screen 156 on the interior of structure 152. During the first few seconds after ignition of the fuel, the flame produced inside support 152 will form on burner screen 156. The other end of catalytic support 152 includes electrically insulative plug 158, through which is disposed spark electrode 170. Spark electrode 170 extends into the interior of catalytic support 152. Any conventional sparking mechanism may be employed, however it is preferred that spark electrode 170 be electrically connected to piezoelectric device 180. Piezoelectric device 180 creates a voltage potential between electrode 170 and catalytic support 152 which can cause a spark suitable for igniting fuel.

Piezoelectric device 180 includes a piezoelectric element or crystal (not shown) which, when compressed along a certain axis, creates a voltage potential across itself. One conductor (not shown) can contact one side of the piezoelectric element and another conductor (not shown) can contact the other side of the piezoelectric element. The two conductors are respectively in electrical contact with spark electrode 170 and catalytic support 152. When the two conductive pieces are squeezed together, the piezoelectric element is compressed in a known manner, and a voltage potential is created across the element. Since the two conductive pieces are in contact with the two ends of the piezoelectric element, the two conductive pieces have the same voltage potential as the two ends of the element when the potential is created. This voltage potential is imparted to spark electrode 170 and catalytic support 152.

When the voltage potential is created and the fuel/air mixture is present inside catalytic support 152, a spark between catalytic support 152 and electrode 170 ignites the fuel/air mixture, and causes a flame front to propagate. Under proper flow conditions, the flame front travels in the opposite direction of the flow of the fuel/air mixture (i.e., from left to right in FIG. 5), until the flame front settles on burner screen 156. The flame heats the catalytic material disposed on the interior of support 152, and catalytic combustion begins.

The size of the flame is small compared to the support, approximately 1/8 inch long. As a result the small portion of support 152 nearest screen 156 temporarily receives most of the heat released by the hot (approximately 1,700° C.), blue, stoichiometric flame. After a short time (1 or 2 seconds), the non-perforated portion of the support receives enough heat by conduction to reach the temperature at which catalytic combustion occurs. As soon as any catalytic activity occurs upstream of the flame, the exhaust products ($CO_2$, $H_2O$, and excess $N_2$) quickly poison the flame and cause it to extinguish. The catalytic reaction is then able to spread over the remainder of the perforated portion of the catalyst, with this reaction taking place at a much lower temperature (400–500° C.) than the flame temperature. This lower temperature allows for a long service life of the catalyst.

The heat-generating catalytic support structure 152 imparts heat to metal plate 130. Metal plate 130 functions similarly to sole plate 32 in the other embodiment. That is, metal plate 130 serves to heat, and thus volatize, a predetermined substance.

Secondary air for combustion enters through secondary air vents 136. As long as the fuel flow is on and constant, the catalytic reaction will continue at a constant rate, and plate 130 will be heated and maintained at a desirable equilibrium temperature. The operation is stopped when the user removes the butane cartridge 200 or when the cartridge runs out of fuel. An on/off switch may be included with the pressure regulator if desired.

In the preferred embodiments, the device of the invention is intended for use with a volatile carrier (not shown) that carries the volatile substance to be dispensed. The carrier is shaped so as to lie in close contact with the heated surface 33 of the sole plate 32 (or plate 130) when placed thereon. Corresponding to the preferred shape of the heated surface 33, the currently preferred shape for the carrier is substantially planar. "Substantially planar" in this context should be understood broadly as including rigid or flexible mats, sheets, or comparable shapes made out of any suitable material that is capable of receiving the volatile substance and then releasing it when heated. A further alternative example of a carrier could be a gel or the like, either having sufficient physical integrity to stand alone or held within a heat-resistive tray. Carriers may be flat, corrugated, pleated, or otherwise formed for convenience, rigidity, or capacity in holding a volatile substance. However, so long as such carriers, taken in gross, present an overall roughly flat appearance when placed on a flat, supporting surface, they shall be understood as being "substantially planar." Desirable materials for such carriers include paperboard, open-pore cellulosic materials, woven cloth and non-woven pads or felts of any suitable fiber, gels, absorbent solid-porous foams, and plastic or ceramic materials capable of releasably receiving the volatile substance.

The device 10 (or device 110) of the invention includes at least one access slot 62, best seen in FIGS. 1 and 2. The access slot 62 is located at a side of the grille 58 and is generally parallel to and at least level with or even slightly above the heated surface 33 of the sole plate 32, preferably extending in length substantially the full dimension of the heated surface at that side. In any event, the access slot 62 has a size such that a volatile carrier of the sort just described may be inserted onto the heated surface 33 or retrieved therefrom through the access slot. The arrangement especially preferred for its convenience includes a pair of access slots 62, one located at each of two, opposite edges of the heated surface 33. By this arrangement, a fresh volatile carrier may be thrust in at one access slot 62 to push the depleted volatile carrier out of the other access slot. This arrangement of access slots 62 is clear from FIGS. 1 and 2.

Preferably, the access slot 62 is sufficiently narrow and has sufficient depth and the sole plate 32 is so located with respect to the access slot that direct contact with the sole plate by the hand of the user is restricted.

Under conditions of use, the device 10 (or device 110) of the invention further includes a volatile substance located on the heated surface 33 of the sole plate 32 (or plate 130). Preferably, the volatile substance is borne upon a carrier resting upon the heated surface 33 in replaceable relation, whereby the volatile substance of the device 10 may be renewed by replacing the carrier. Carriers of the sort described above and utilized with devices having access slots 62, as described above, are preferred embodiments of the invention so defined.

A preferred volatile substance is an insect control active ingredient. "Insect control active ingredient" shall be understood to include a material capable of repelling, killing, or otherwise interfering with the activity of insects. Examples include pyrethroids, such as pynamin-forte, a pyrethroid sold by the Sumitomo Company.

Volatile substances useful as air treatment materials, including air fresheners and the like, include any of a number of scented materials.

Preferably, the housing 46 encloses not only the heat box 42 but also the fuel tank 12, tank connection means 16, and the rest of the working parts described above. This arrangement is shown in FIGS. 1–3. Such a preferred form of the housing 46 provides a convenient structure to hold control buttons such as the first and second control buttons shown respectively at 64 and 66. The first control button 64 shown in the preferred embodiment operates to permit gas to flow at a predetermined fixed rate from the fuel tank through the pressure regulator 19. The pressure regulator may be adapted by various conventional linkages to control gas flow and therefore the size and heat of the resulting flame at the combustion nozzle 20 under control of control button 64 by providing controllable movement by the button to control the pressure in the regulator 19 to adjust gas flow. The second control button shown at 66 of the preferred embodiment activates the piezoelectric igniter 30. These particular control arrangements are only examples of what is possible, of course, and the invention should not be understood as in any way limited to them. (These controls are also usable with the embodiment of FIG. 5.). Especially when this preferred form of the housing 46 is used, the housing includes at least one air intake duct 67 to provide a source of fresh air to feed the flame of the combustion nozzle 20 and to generally ventilate the housing. The air intake ducts 67 are best seen in FIGS. 1 and 3. An access cover 68 is provided to allow a user to gain access to and replace the fuel tank 12. The access cover 68 is adapted to be replaceably removed from the housing 46 by finger pressure activation of a conventional latch arrangement, such as the latch shown at 70 in FIG. 3.

Feet 72 are provided beneath the housing 46 to elevate the housing above any flat surface on which it may be placed. This elevation insures that air can flow freely in through the housing vents 56 and air intake ducts 67, if they are located in the underside of the housing 46, as is preferred in the embodiment shown. The feet 72 provide the further advantage of reducing temperature buildup beneath the device 10.

The method of the invention for dispensing a volatile substance into the air includes the steps of providing a gas-fueled, portable heat source adapted to fuel a flame at a combustion nozzle. The method further includes providing a sole plate having a heated surface for heating the substance to be volatilized. Preferably, the heated surface is maintainable at a temperature within the range of from about 50 to 280° C. and more preferably from about 125 to 200° C. The method of the invention further includes providing heat transfer means for transferring heat from the flame of the combustion nozzle to the sole plate. A further step includes providing a heat box that substantially surrounds the heat transfer means and sole plate, the heat box being made of materials capable of withstanding the heat radiating therefrom and having a window through which volatile substances may escape the heat box. By these steps, a flame may be sustained at the combustion nozzle to heat the sole plate and volatilize volatile substance placed on the heated surface of the sole plate. The volatilized material may then escape through the heat box window to be dispensed into the atmosphere.

The method of the invention may, alternatively, include providing a gas-fueled, portable heat source adapted to fuel flameless combustion on a catalytic heater, as described above. By such a method, flameless combustion may be sustained on the catalytic heater to heat the heating plate and volatilize a substance placed on the heated surface of the heating plate. The volatilized material may then escape through the heat box window to be dispensed into the atmosphere.

The method of the invention preferably includes the further step of providing a housing having interior surfaces that define an interior chamber within which the heat box is held in spaced relation from the housing, the housing including a housing window that is adjacent to and preferably open above the heat box window. By this step, a housing is provided that may remain cool relative to the temperature of the flame, the heat transfer means, and the sole plate (or, alternatively, relative to the temperature of the catalytic heater and the heating plate).

A further preferred step of the invention is to apply a volatile substance to the heated surface of the sole or heating plate, wherein the volatile substance is selected from the group consisting of insect control active ingredients, air treatment materials, and combinations thereof. Preferably, the volatile substance is an insect control active ingredient.

Preferably the heat transfer means is made of heat conductive material and includes a combustion chamber that substantially encloses the combustion nozzle and any flame burning at the combustion nozzle, the combustion chamber being connected to the sole plate in thermally conductive relation. Preferably the combustion chamber has heat-conductive chamber walls, at least one pressure release port extending through the chamber walls, and a flame arrester to prevent escape of flame from the combustion chamber while simultaneously allowing the substantially unobstructed passage of air through the pressure release port. Of course, in the embodiment of the method utilizing a catalytic heater, the catalytic heater is self-flame arresting and no separate flame arrester is needed. Moreover, in the embodiment of the method utilizing a catalytic heater, a separate combustion chamber need not be provided, and the heat transfer means may at least partially surround the catalytic heater.

Preferably the heat box window is closed with an air-transmitting grille that is spaced from the heated surface of the sole plate sufficiently far as to withstand the heat therefrom but is spaced close enough to be heated sufficiently that volatile substance leaving the heated surface does not condense on the grille.

It is preferred that the method of the invention further includes supplying the volatile substance to be dispensed borne by a substantially planar carrier adapted to be held on and heated by the heated surface of the sole or heating plate. It is preferred also to provide at least one access slot located at a side of the grille and generally parallel to and at least level with the heated surface of the sole or heating plate, the access slot having a size such that a volatile carrier may be inserted onto the heated surface or retrieved therefrom through the access slot.

The non-metal parts of the device 10 of the invention may be conveniently manufactured of suitable plastics or ceramics by conventional molding techniques. Metal parts may be made by conventional methods, including extrusion. The volatile carriers described may be made by impregnating the carrier materials referred to above by various impregnation techniques well known to those skilled in the art, including but not limited to simply wetting the carrier materials with a solution of the volatile substances to be dispensed and allowing the solution to dry.

INDUSTRIAL APPLICABILITY

The effective dispensing of volatile substances into the air is industrially applicable to insect control, as well as to air treatment for odors and other purposes. The portability of the device 10 of the invention is immediately applicable under any condition of use but is especially valuable in outdoor and other locations where electrical power is not easily available.

While preferred embodiments of the invention have been shown in the drawings and has been described, variations in the preferred form, which will be apparent to those skilled in the art, are within the scope and breadth of the invention. Consequently, the invention should not be construed as limited to the specific preferred embodiments shown and described but, instead, should be understood in terms of the following claims.

We claim:

1. A device for dispensing a volatile substance comprising
   a. a portable heat source having tank connection means connectable with a fuel tank in gas-tight relation, a catalytic heater, and means for metering fuel under pressure from the fuel tank to the catalytic heater to fuel flameless combustion at the catalytic heater;
   b. a heating plate having a heated surface for heating the volatilizable substance, said heating plate receiving heat from said catalytic heater;
   c. a heat box substantially surrounding the catalytic heater and heating plate, the heat box being made of materials capable of withstanding the heat radiating therefrom and having a window, through which volatile substances released from the heating plate may escape the heat box; and
   d. a housing having interior surfaces that define an interior chamber within which the heat box is held in spaced relation from the housing, the housing including a housing window that is adjacent to the heat box window;

wherein flameless combustion may be sustained on the catalytic heater to heat the heating plate to volatilize a volatile substance placed on the heated surface, which volatilized substance may then escape into the atmosphere through the heat box window, with the housing remaining cool relative to the temperature of the catalytic heater and the heating plate.

2. The device of claim 1 wherein the fuel tank is replaceable so that the device may be refueled by removing a depleted tank and substituting a full tank.

3. The device of claim 1 wherein the volatile substance is selected from the group consisting of insect control active ingredients, air treatment materials, and combinations thereof.

4. The device of claim 1 wherein the heat box includes at least one heat box vent at a location lower than the heat box window, and the housing includes a housing vent at a location no higher than the level of the heat box vent, the housing vent so offset from the heat box vent that straight-line access through the vents to the heat transfer means is restricted, whereupon a convection current is generated as a result of catalytic combustion, aiding in the escape of volatilized substances from the heat box window.

5. The device of claim 1, wherein said heating plate at least partially surrounds said catalytic heater.

6. A device for dispensing a volatile substance according to claim 5, wherein said heating plate comprises a channel and said catalytic heater is disposed in said channel.

7. A device for dispensing a volatile substance according to claim 5, wherein said heating plate comprises a top plate, two side plates, and a bottom plate which substantially surround and enclose said catalytic heater.

8. The device of claim 1 wherein the heat box window is closed with an air-transmitting grille that is spaced above the heated surface of the heating plate sufficiently far as to withstand the heat therefrom but close enough to be heated sufficiently that volatilized substances leaving the heated surface do not condense on the grill.

9. The device of claim 8 for use with a substantially planar volatile carrier carrying the volatile substance to be dispensed, the device including at least one access slot located at a side of the grille and generally parallel to and at least level with the heated surface of the heating plate, the access slot having a size such that a volatile carrier may be inserted or retrieved therethrough.

10. The device of claim 9 wherein the access slot is sufficiently narrow and has sufficient depth and the heating plate is so located with respect to the access slot that direct contact with the heating plate by the hand of a user is restricted.

11. The device of claim 1 further comprising a volatile substance located on the heated surface of the heating plate.

12. The device of claim 11 wherein the volatile substance is borne upon a carrier resting upon the heated surface in replaceable relation, whereby the volatile substance of the device may be renewed by replacing the carrier.

13. The device of claim 12, wherein the carrier is made of a substance selected from the group consisting of paper-board, open-pore cellulosic materials, woven cloth and non-woven pads or felts of any suitable fiber, gels, absorbent solid-porous foams, and plastic or ceramic materials capable of releasably receiving the volatile substance.

14. The device of claim 11 wherein the volatile substance is an insect control active ingredient.

15. The device of claim 1 wherein the temperature of the heating plate is maintainable within a temperature range of from about 125 to 200° C.

16. A device for dispensing a volatile substance according to claim 1, wherein said catalytic heater comprises a flame arrester for preventing any flame created during an ignition phase of combustion from exiting said device.

17. A device for dispensing a volatile substance according to claim 1, wherein said fuel tank is refillable.

18. A method for dispensing a volatile substance into the atmosphere comprising the steps of:
   a. providing a gas-fueled, portable heat source adapted to fuel flameless combustion on a catalytic heater;
   b. providing a heating plate having a heated surface for heating the substance to be volatilized, said heating plate receiving heat from said catalytic heater;
   c. providing a heat box that substantially surrounds the catalytic heater and heating plate, the heat box being made of materials capable of withstanding the heat radiating therefrom and having a window through which volatile substances from the heating plate may escape the heat box;

wherein flameless combustion may be sustained on the catalytic heater to heat the heating plate and volatilize volatile substance placed on the heated surface, which may then escape through the heat box window to be dispensed into the atmosphere.

19. The method of claim 18 further including the step of providing a housing having interior surfaces that define an interior chamber within which the heat box is held in spaced relation from the housing, the housing including a housing window located adjacent to the heat box window, whereby the housing may remain cool relative to the temperature of the catalytic heater and the heating plate.

20. The method of claim 18 including the further step of applying a volatile substance to the heated surface of the heating plate, the volatile substance being selected from the group consisting of insect control active ingredients, air treatment materials, and combinations thereof.

21. The method of claim 18 including the further step of supplying the volatile substance to be dispensed borne by a substantially planar volatile carrier adapted to be held on and heated by the heated surface.

22. The method of claim 18 wherein the heat box window is closed with an air-transmitting grille that is spaced above the heated surface of the heating plate sufficiently far as to withstand the heat therefrom but is spaced close enough to be heated sufficiently that volatile substance leaving the heated surface does not condense on the grille.

23. The method of claim 18 including the further step of providing at least one access slot located at a side of the grille and generally parallel to and at least level with the heated surface of the heating plate, the access slot having a size such that a volatile carrier may be inserted onto the heated surface or retrieved therefrom through the access slot.

24. The method of claim 18 wherein the temperature of the heating plate is maintainable within the range of from about 125 to 200° C.

25. A device for dispensing a volatile substance, said device comprising:
   a housing,
   a portable heating appliance carried in said housing, said portable heating appliance comprising a source of butane gas, and heat means having a temperature related to the amount of said butane gas flowing to said heat means, said butane gas flowing in a stream,
   a pad of material containing said volatile substance, said pad carried on a compartment proximate said heat exchanger, and
   a metal plate receiving heat from said heat means to be heated thereby and causing said pad of material to be heated,
   said heat means and said metal plate providing air flow caused by said butane gas flowing in said stream to pass around said pad of material to heat, carry and disperse the volatile substance in said pad,
   wherein said housing remains cool relative to the temperature of said heat means and said metal plate.

26. A device for dispensing a volatile substance according to claim 25, wherein said heat means comprises a catalytic heater, said butane gas flowing to said catalytic heater to be flamelessly combusted as said heat means.

27. A device for dispensing a volatile substance according to claim 26, wherein said heat means comprises a regulator to control the rate of flow of butane gas.

28. A device for dispensing a volatile substance according to claim 27, wherein said regulator is adjustable by the user to adjust the heat of said heat means.

29. A device for dispensing a volatile substance according to claim 25, wherein said heat means comprises a regulator to control the rate of flow of butane gas.

30. A device for dispensing a volatile substance according to claim 29, wherein said regulator is adjustable by the user to adjust the heat of said heat means.

31. A device for dispensing a volatile substance according to claim 25, wherein said metal plate at least partially surrounds said catalytic heater.

32. A device for dispensing a volatile substance according to claim 31, wherein said metal plate comprises a channel and said catalytic heater is disposed in said channel.

33. A device for dispensing a volatile substance according to claim 31, wherein said metal plate comprises a top plate, two side plates, and a bottom plate which substantially surround and enclose said catalytic heater.

34. A device for dispensing a volatile substance according to claim 25, wherein said catalytic heater comprises a flame arrester for preventing any flame created during an ignition phase of combustion from exiting said device.

35. A device for dispensing a volatile substance according to claim 34, wherein said catalytic heater comprises:
   an enclosed structure having first and second ends;
   an opening at said first end adapted to receive fuel;
   an ignition source mounted on one of said first and second ends extending into an interior of said structure;
   a burner nozzle disposed in an interior of said structure; and
   catalytically active material provided on a surface of said structure,
   wherein, by placing said ignition source in said interior of said structure, said structure acts as said flame arrester.

36. A device for dispensing a volatile substance according to claim 16, wherein said catalytic heater comprises:
   an enclosed structure having first and second ends;
   an opening at said first end adapted to receive fuel;
   an ignition source mounted on one of said first and second ends extending into an interior of said structure;
   a burner nozzle disposed in an interior of said structure; and
   catalytically active material provided on a surface of said structure,
   wherein, by placing said ignition source in said interior of said structure, said structure acts as said flame arrester.

* * * * *